(12) United States Patent
Summer et al.

(10) Patent No.: US 11,649,501 B2
(45) Date of Patent: May 16, 2023

(54) BIOMARKER FOR DETECTING A POSSIBLE INCOMPATABILITY WITH RESPECT TO METAL IMPLANTS

(71) Applicant: KLINIKUM DER UNIVERSITAET MUENCHEN, Munich (DE)

(72) Inventors: Burkhard Summer, Munich (DE); Peter Thomas, Augsburg (DE); Sylvia Usbeck, Leipzig (DE); Diana Lill, Munich (DE)

(73) Assignee: KLINIKUM DER UNIVERSITAET MUENCHEN, Munich (DE)

( * ) Notice: Subject to any disclaimer, the term of this patent is extended or adjusted under 35 U.S.C. 154(b) by 108 days.

(21) Appl. No.: 16/971,692

(22) PCT Filed: Feb. 4, 2019

(86) PCT No.: PCT/DE2019/200006
§ 371 (c)(1),
(2) Date: Nov. 2, 2020

(87) PCT Pub. No.: WO2019/161853
PCT Pub. Date: Aug. 29, 2019

(65) Prior Publication Data
US 2021/0054460 A1  Feb. 25, 2021

(30) Foreign Application Priority Data
Feb. 23, 2018 (DE) .................. 10 2018 104 133.0

(51) Int. Cl.
C12Q 1/68 (2018.01)
C12P 19/34 (2006.01)
C12Q 1/6883 (2018.01)

(52) U.S. Cl.
CPC ..... C12Q 1/6883 (2013.01); *C12Q 2600/156* (2013.01)

(58) Field of Classification Search
CPC .......... C12Q 21/6883; C12Q 2600/156; C12Q 2600/172
See application file for complete search history.

(56) References Cited

FOREIGN PATENT DOCUMENTS

WO   WO 2009/067473 A2   5/2009

OTHER PUBLICATIONS

Anna Ryberg, et al., "Concurrent genotyping of Helicobacter pylori virulence genes and human cytokine SNP sites using whole genome amplified DNA derived from minute amounts of gastric biopsy specimen DNA", BMC Microbiology 2008, 8:175. (Year: 2008).*
Amine El-Mokhtar Drici, et al., "Effect of IL-1 b and IL-1RN polymorphisms in carcinogenesis of the gastric mucosa in patients infected with Helicobacter pylori in Algeria", Libyan Journal of Medicine (2016) 11:31576. (Year: 2016).*
TP Chaturvedi. "Allergy related to dental implant and its clinical significance" Clin Cosmet Investig Dent. 2013; 5: 57-61. (Year: 2013).*
Rachael M. Dewberry, et al., "Interleukin-1 Receptor Antagonist (IL-1RN) Genotype Modulates the Replicative Capacity of Human Endothelial Cells" Circulation Research, 2003; 92:1285-1287. (Year: 2003).*
H. Jansson et al.: "Clinical Consequences of IL-1 Genotype on Early Implant Failures in Patients under Periodontal Maintenance", Clinical Implant Dentistry and Related Research, vol. 7, No. 1, pp. 51-59 (2005).
M. H. A. Malik et al.: "Genetic susceptibility to total hip arthroplasty failure: a preliminary study on the influence of matrix metalloproteinase 1, interleukin 6 polymorphisms and vitamin D receptor", Annals of the Rheumatic Diseases, , vol. 66, No. 8, pp. 1116-1120 (2007).
C. C. Montes et al.: "Analysis of the association of IL1B (C+3954T) and IL1RN (intron 2) polymorphisms with dental implant loss in a Brazilian population", Clinical Oral Implants Research, vol. 20, No. 2, pp. 208-217 (2009).
M. Sampaio Fernandes et al.: „The role of IL-1 gene polymorphisms (IL1A, IL1B, and IL1RN) as a risk factor in unsuccessful implants retaining overdentures, Journal of Prosthodontic Research, vol. 61. No. 4, pp. 439-449 (2017).
C. Pérez-Ramìrez et al.: "Interleukins as new prognostic genetic biomarkers in non-small cell lung cancer", Surgical Oncology, Blackwell Scientific Publ., vol. 26, No. 3, pp. 278-285 (2017).

(Continued)

*Primary Examiner* — Stephen T Kapushoc
(74) *Attorney, Agent, or Firm* — Norman B. Thot

(57) ABSTRACT

A method to predict an increased risk of a greater susceptibility to a metal implant sensitivity in a test person. The method includes providing an isolated sample with a genetic material of the test person, and examining a single nucleotide polymorphism rs1143627

```
                                            SEQ ID NO: 1
AGCCTCCTACTTCTGCTTTTGAAAGC[C/T]ATAAAA

ACAGCGAGGGAGAACTGG,
``` in a gene coding for interleukin 1 beta and ascertaining whether a C is present at a position of the single nucleotide polymorphism, and/or examining a VNTR polymorphism rs2234663 with the repeat

```
                                            SEQ ID NO: 2
ATCCTGGGGAAAGTGAGGGAAATATGGACATCACATGGAACAACAT

CCAGGAGACTCAGGCCTCTAGGAGTAACTGGGTAGTGTGC,
``` in a gene coding for a IL1 receptor antagonist, IL1-RN and ascertaining whether the repeat is present five times.

4 Claims, No Drawings
Specification includes a Sequence Listing.

(56) References Cited

OTHER PUBLICATIONS

S. Ramírez-Pérez et al.: "Association of 86 bp variable number of tandem repeat (VNTR) polymorphism of interleukin-1 receptor antagonist (IL1RN) with susceptibility and clinical activity in rheumatoid arthritis", Clinical Rheumathology, Acta Medica Belgica, vol. 36, No. 6, pp. 1247-1252 (2017).

E. Jacobi-Gresser et al.: „Genetic and immunological markers predict titanium implant failure: a retrospective study., Int. J. Oral Maxillofac. Surg., vol. 42, No. 4, pp. 537-543 (2013).

E. Jacobi-Gresser: "Prognose der Einheilquote von Titanimplantaten anhand von Laborparametern—eine retrospektive Studie", umwelt-medizin-gesellschaft, vol. 26, pp. 98-103, English Translation (2013).

Y.-H. Liu et al.: "Association of Interleukin-1β (IL1B) Polymorphisms with Graves' Ophthalmopathy in Taiwan Chinese Patients", Investigative Ophthalmology & Visual Science, vol. 51, No. 12, pp. 6238-6246 (2010).

P. F. Sharkey et al.: "Why are Total Knee Arthroplasties Failing Today—Has Anything Changed After 10 Years?", The Journal of Arthroplasty. vol. 29, pp. 1774-1778 (2014).

M. Thomsen et al.: "Adverse Reaktionen gegenüber orthopädisch-chirugischen Metallimplantaten nach Kniegelenkersatz.", Der Hautarzt 5, vol. 67, pp. 347-351 (2016), English Translation.

D. Granchi et al.: "Sensitivity to Implant Materials in Patients Undergoing Total Hip Replacement.", Wiley Periodicals, Inc. J Biomed Mater Res Part B: Appl Biomater, vol. 77B, pp. 257-264 (2006).

P. Thomas et al.: "Diagnosis and management of patients with allergy to metal implants.", Expert Review of Clinical Immunology, vol. 11:4, pp. 501-509 (2015).

G. Stucki et al.: "Evaluation of a German version of the WOMAC (Western Ontario and McMaster Universities)", osteoarthritis index,. Z Rheumatol, vol. 55, pp. 40-49 (1996), English Translation.

A. Schnuch et al.: "Patch testing with contact allergens", Guideline of the German Dermatologic Society (Deutsche Dermatilogische Gesellschaft, DDG) and the German Society for Allergy and Clonical Immunology (Deutsche Gesellschaft für Allergie und klinische Immunologie. DGAKI), JDDG, vol. 6, pp. 770-775 (2008), English Version.

B. Summer et al.: "Nickel (Ni) allergic patients with complications to Ni containing joint replacement show preferential IL-17 type reactivity to Ni", Contact Dermatitis, vol. 63, pp. 15-22 (2010).

H. M. Colhoun et al.: "Problems of reporting genetic associations with complex outcomes", The Lancet, vol. 361, pp. 865-872 (2003).

H. T. Yang et al.: "Association of interleukin gene polymorphisms with the risk of coronary artery disease", Genetics and Molecular Research, vol. 14(4), pp. 12489-12496 (2015).

R. Lopéz-Mejías et al.: "Interleukin 1 beta (IL1β) rs16944 genetic variant as a genetic marker of severe renal manifestations and renal sequelae in Henoch-Schönlein purpura", Clinical and Experimental Rheumatology, vol. 34 (Suppl 97), pp. 84-88 (2016).

J. T. Den Dunnen et al.: "HGVS Recommendations for the Description of Sequence Variants: 2016 Update", Human Mutation, vol. 37, pp. 564-569 (2016).

* cited by examiner

BIOMARKER FOR DETECTING A POSSIBLE INCOMPATABILITY WITH RESPECT TO METAL IMPLANTS

CROSS REFERENCE TO PRIOR APPLICATIONS

This application is a U.S. National Phase application under 35 U.S.C. § 371 of International Application No. PCT/DE2019/200006, filed on Feb. 4, 2019 and which claims benefit to German Patent Application No. 10 2018 104 133.0, filed on Feb. 23, 2018. The International Application was published in German on Aug. 29, 2019 as WO 2019/161853 A1 under PCT Article 21(2).

FIELD

The present invention relates to a method and to a kit to predict an increased risk of greater susceptibility to metal implant sensitivity.

BACKGROUND

Implants are increasingly playing an important role, for example, in orthopedics and dentistry. Such implants are frequently made of metal, for example, of pure titanium or metal alloys. Concomitant therewith is, however, an increase in the number of implant allergic reactions [1-4]. Even small quantities of impurities or foreign materials in the metal, e.g., nickel, can, for example, lead to an inflammatory or an allergic response. Wear particles, which are absorbed by macrophages and monocytes, or corrosion processes can also trigger inflammatory responses. Complications are also observed where endoprostheses are used which cannot be attributed to known causes such as products of corrosion, wear or infection. As yet puzzling hyper-inflammatory responses have been observed which can be accompanied, for example, by swelling, recurrent joint effusions, pain, limited movement, a loosening or failure of an implant.

JACOBI-GRESSER, E. et al. (Genetic and immunological markers predict titanium implant failure: a retrospective study, Int. J. OralMaxillofac. Surg. (2013) 42 (4) 537-543) describes an evaluation of diagnostic markers to predict the failure of titanium implants. The result of the implant was assessed for 109 test subjects who had undergone titanium implant surgery, IL1A-889 C/T (rs1800587), IL1B+3954 C/T (rs1143634), IL1RN+2018 T/C (rs419598), and TNFA-308 G/A (rs1800629) genotyping, in-vitro IL-1β/TNF-α secretion tests, and lymphocyte transformation tests during the treatment.

RAMIREZ-PEREZ, S. et al. (Association of 86 bp variable number of tandem repeat (VNTR) polymorphism of interleukin-1 receptor antagonist (IL1RN) with susceptibility and clinical activity in rheumatoid arthritis, Clin. Rheumatol. (2017) 36 (6) 1247-1252) describes that several studies have a variable number of tandem repeats (VNTR) 86 bp (rs2234663) in the intron 2 of the IL1RN gene with rheumatoid arthritis (RA) risk. The aim of this study was to determine the frequency of this polymorphism in patients with RA and control subjects (CS), and its association with RA in a western Mexican population. An analytical cross-sectional study was undertaken involving 350 patients with RA and 307 CS. The IL1RN VNTR polymorphism was identified by means of polymerase chain reaction (PCR) and genotypes were associated with clinical variables (DAS28 and CRP).

JACOBI-GRESSER, E. (Prognose der Einheilquote von Titanimplantaten anhand von Laborparametern-eine retrospektive Studie. umweltmedizin-gesellschaft 26 (February 2013) 98-103) describes an assessment of diagnostic markers for the prediction of titanium implant failure. The result of the implant was assessed retrospectively for 109 test subjects who had undergone a titanium implant operation, IL1A-889 C/T (rs1800587), IL1B+3954 C/T (rs1143634), IL1RNN+2018 T/C (rs419598), and TNFA-308 G/A (rsl 800629) genotyping, in vitro IL-1 ß/TNF-a secretion tests, and lymphocyte transformation tests during the treatment. TNF-a and IL-1ß secretion in response to titanium stimulation were significantly higher in the patients with implant failure (TNF-a: 256.89 pg/ml vs. 81.4 pg/ml); p<0.0001; IL-1ß: 159.96 pg/ml vs. 54.01 pg/ml; p<0.0001).

LIU, Y. H. et al. (Association of interleukin-1beta (IL1B) polymorphisms with Graves' ophthalmopathy in Taiwan Chinese patients, Invest. Ophthalmol. Vis. Sci. (2010) 51 (12) 6238-46) describes an investigation as to whether variations in the IL1B gene can be associated with Graves' ophthalmopathy (GO) in patients with Morbus Basedow (GD). In the IL1B-SNPs examined, the C allele of rs1143634 was associated with GD, whereas the T/T genotype of the SNPs rs1143634 and rs16944 was associated to a lesser extent with the disease. The A/A genotype of the SNPs rs3917368 and rs1143643, which had the strongest interaction, can increase the risk of GO (P=0.024 and P=0.017, respectively). Several GD susceptible and insusceptible haplotypes IL1B have been identified, and the Ht4-GCGCCTCC haplotype, which is composed of eight SNPs and is associated with low circulating IL1β values, can protect against developing GO (P=0.025). The data for IL1B polymorphisms and the association of GD and GO with the plasma IL1β indicate that IL1B polymorphisms can be associated with the development of GD and GO.

SUMMARY

An aspect of the present invention is to improve the prediction of possible complications when using metal implants.

In an embodiment, the present invention provides a method to predict an increased risk of a greater susceptibility to a metal implant sensitivity in a test person. The method includes providing an isolated sample with a genetic material of the test person, and at least one of examining a single nucleotide polymorphism rs1143627

```
                                          SEQ ID NO: 1
   AGCCTCCTACTTCTGCTTTTGAAAGC[C/T]ATAAAAACA

GCGAGGGAGAACTGG,
``` in a gene coding for interleukin 1 beta and ascertaining whether a C is present at a position of the single nucleotide polymorphism, and examining a VNTR polymorphism rs2234663 with the repeat

```
                                          SEQ ID NO: 2
   ATCCTGGGGAAAGTGAGGGAAATATGGACATCACATGGAACAAC

ATCCAGGAGACTCAGGCCTCTAGGAGTAACTGGGTAGTGTGC,
``` in a gene coding for a IL1 receptor antagonist, IL1-RN and ascertaining whether the repeat is present five times.

SEQUENCE LISTING

The Sequence Listing associated with this application is filed in electronic form via EFS-Web and is hereby incorporated by reference into this specification in its entirety. The name of the text file containing the Sequence Listing is Sequence_Listing_AJMUN2001. The size of the text file is 4,818 Bytes, and the text file was created on Aug. 20, 2020.

DETAILED DESCRIPTION

The present invention provides a method to predict an increased risk of greater susceptibility to metal implant sensitivity in a test person, whereby in an isolated sample with genetic material of the test person:
a) a single nucleotide polymorphism rs1143627

```
                                   SEQ ID NO: 1
    AGCCTCCTACTTCTGCTTTTGAAAGC[C/T]

ATAAAAACAGCGAGGGAGAACTGG,
``` in the gene coding for interleukin 1 beta, is examined and it is ascertained whether a C is present at the position of the single nucleotide polymorphism and/or
b) a VNTR polymorphism rs2234663 with the repeat

```
                                        SEQ ID NO: 2
    ATCCTGGGGAAAGTGAGGGAAATATGGACATCACATGGAACAAC

ATCCAGGAGACTCAGGCCTCTAGGAGTAACTGGGTAGTGTGC,
``` in the gene coding for the IL1 receptor antagonist, IL1-RN, is examined and it is ascertained whether the repeat is present five times.

It has surprisingly proved to be the case that the polymorphisms rs1143627 and rs2234663 are suitable as biomarkers for the determination of a possible increased risk that a person who is due to receive or has already received a metal implant will develop a sensitivity to the implant. It can be assumed that the risk is higher when the single nucleotide polymorphism has rs1143627 C and not T at the position of the single nucleotide polymorphism, and/or when the VNTR polymorphism rs2234663 has the repeat five times in tandem one after the other. The sensitivity can particularly manifest itself in a greater inflammation susceptibility, leading to a loosening of the implant (with osteolysis), pain, effusions, deterioration in function (e.g., reduced movement of joint prostheses).

Without wanting to be bound to one particular theory, it is assumed that the biomarkers indicate a genetically determined disequilibrium of the inflammation regulation. This leads to sensitivity in response to the "foreign body" implant. The human immune system reacts to different individual degrees to one and the same inflammatory stimulus (e.g., bacteria, implant materials), the development of the immune response being determined by the ratio of pro- and anti-inflammatory mediators (e.g., cytokines) which play a significant role in the defense mechanism. Cytokine IL-1 is one of the most important pro-inflammatory mediators. Hypersecretion of this mediator resulting from a genetically determined polymorphism can, for example, lead to an overreaction of the immune system. The pro-inflammatory effect of IL-1 is normally down-regulated by the antagonist IL-RN. However, when a suppressive polymorphism is here also present, there is insufficient inhibition of the inflammation to counteract the inflammatory mediator IL-1, which can result in a hyper-inflammatory response. This can go at least some way to explaining cases where there is a strong, inflammatory response to an implant with no apparent cause.

In a person who needs an implant, the method according to the present invention can serve, for example, to ascertain before the implantation takes place whether in this case there is a higher probability that complications, especially hyper-inflammatory responses, must be expected if a metal implant is used. It is possible in such a case to switch to a different implant material, e.g., ceramic. The present invention can be advantageous not only in orthopedics or endoprosthetics, for example, but also for dental implants.

The term "greater susceptibility to metal implant sensitivity" means a higher probability than the average total population of a sensitivity response, especially an inflammatory response, to a metal implant.

An "implant" or an "endoprosthesis" means a synthetic material implanted into the body which is intended to remain there on a permanent basis or at least for a longer period of time. Examples of implants are hip joint, knee joint, shoulder joint or dental implants. The term also covers osteosyntheses such as plates, pins, or screws, which are implanted in the body.

A "metal implant" in this context means a cobalt-chrome-molybdenum-based, stainless steel-based or a titanium implant, especially as a hip/knee prosthesis or dental implant.

The term "arthroplasty" (also known as "alloarthroplasty") is used here especially in relation to the use of joint endoprostheses, i.e., the replacement of one or more joint surfaces with allogeneic, i.e., exogenous, non-biological material.

The term "polymorphism" refers to sequence variations in the genes of a population. Such sequence variations can cause different individuals of a population or also different cells of an individual to exhibit different variants of a certain gene at the same locus, and are also called "alleles". The term covers variations in individual nucleotides (SNVs or SNPs), or, for example, the occurrence of a different number of sequence repeats (e.g., mini-satellite sequences, VNTRs).

The term "single nucleotide polymorphism rs1143627" (possibly also referred to as IL-1B-31) in this context refers to a polymorphism affecting one single nucleotide at the position −31 (relative to the start codon) in the promoter region of the gene coding for interleukin 1 beta (IL-1B, IL-1β), whereby a C or a T can be located at the position (e.g., NG_008851.1: g.4970C>T as per HGVS Nomenclature Recommendation, c.f. [11]). A sequence of the region in question with the single nucleotide variation (SNV) is presented below:

```
                                         (SEQ ID NO: 1)
    AGCCTCCTACTTCTGCTTTTGAAAGC[C/T]

ATAAAAACAGCGAGGGAGAACTGG
```

The possible nucleotide variants (here C or T) are given in square brackets. Instead of the expression "single nucleotide variation" or SNV, the term "single nucleotide polymorphism" or SNP is sometimes also used synonymously.

The term "VNTR polymorphism rs2234663" (possibly also referred to as "intron 2 VNTR rs2234663" or "intron 2 VNTR") means a polymorphism with a variable number (2-6) of tandem-like sequential repeats (VNTR, variable number tandem repeat) with the sequence (SEQ ID NO: 2)
ATCCTGGGGAAAGTGAGGGAAATATGGACATCACATGGAACAA

CATCCAGGAGACTCAGGCCTCTAGGAGTAACTGGGTAGTGTGC present in the gene which codes for the IL1 receptor antagonist (IL1-AN or IL1-RN). A sequence with four repeats appears, for example, in the LRG sequence (LRG=Locus Reference Genomic sequence) LRG_188, (c.f. http://ftp.ebi.ac.uk/pub/databases/lrgex/LRG_188.xml; c.f. also NCBI reference sequence with the accession version NG_021240.1). According to the HGVS Nomenclature Recommendation (c.f. [11]), the VNTR polymorphism with five repeats would be referred to as g.17637_17722 [5].

The term "atopic disease" means a disease which is based on a genetically determined readiness to react to aerogenic, gastrointestinal, or cutaneous contact with natural or synthetic substances from the environment with an allergic reaction of the immediate type (Type I allergy), i.e., to react with an enhanced formation of IgE. Atopic diseases frequently involve the interfaces of the respiratory and gastrointestinal mucous membranes, and the skin. Examples for an atopic disease are allergic bronchial asthma, allergic rhinitis (allergic rhinoconjunctivitis), and atopic dermatitis (atopic eczema, neurodermatitis).

With the method according to the present invention of VNTR polymorphism rs2234663 with the repeat

SEQ ID NO: 2
ATCCTGGGGAAAGTGAGGGAAATATGGACATCACATGGAACAA

CATCCAGGAGACTCAGGCCTCTAGGAGTAACTGGGTAGTGTGC, in the gene coding for the IL1 receptor antagonist, IL1-RN, it can, for example, be examined and ascertained whether the repeat is present five times.

With the method according to the present invention, it can, for example, additionally be determined whether the test person also has an atopic disease. Examples of atopic diseases are bronchial asthma, allergic rhinoconjunctivitis, and atopic dermatitis. Especially when there is a combination of the presence of a VNTR polymorphism rs2234663 with five repeats and an atopic disease, it can be concluded that there is an increased risk that the person concerned will suffer complications, especially hyper-inflammatory responses, when a metal implant is implanted.

The present invention also relates to a kit to perform the method according to the present invention. The kit according to the present invention comprises the primer sequences in Table 1:

TABLE 1

| Polymorphism | Primer Sequences | SEQ ID NO | Annealing Temperature |
|---|---|---|---|
| 1L-1B-31 (rs1143627) | TCTTTTCCCCT TTCCTTTAACT | 10 | 52° C. |
| | GAGAGACTCCC TTAGCACCTAGT | 11 | |
| IL-1RN intron 2 VNTR (rs2234663) | CCCCTCAGC AACACTCC | 12 | 65° C. |
| | GGTCAGAAG GGCAGAGA | 13 | |

The present invention is described in greater detail below using example embodiments purely for illustration purposes.

A study was carried out involving 195 patients with total endoprostheses who had given their consent after being provided with full details. The study was approved by the local ethics committee and registered under the study ID 230-12 at ClinicalTrials.gov.

102 patients (72 female, 30 male, 41-81 years old) had arthroplasties with complications. The control group consisted of 93 patients (70 female, 23 male, 18-96 years old) with normally functioning arthroplasties.

Questionnaires

A questionnaire-supported case history was compiled containing information about smoking, medication taken, type of implant, metal allergy case history, and the case history of atopic diseases such as allergic rhinitis, atopic eczema, or asthma. The orthopedic WOMAC questionnaire (Western Ontario and McMaster Universities Osteoarthritis Index, WOMAC) was used to quantify the self-assessment of the patient as to the behavior of the artificial joint in respect of pain, stiffness, and impairment of function [5].

Allergens and Patch Tests

All patients were allergy tested via a patch test. Almirall-Hermal patch test preparations and Finn Chambers on Scanpor (Almirall Hermal, Reinbek, Germany) were used therefor. The substances were applied onto the upper back on Day 0. The standard series with 29 allergens, a routine additional series, and a bone cement series (when the patients in question had a cemented endoprosthesis) in accordance with the guidelines of the German Contact Dermatitis Research Group (DKG) were tested [6]. The measurements were performed by doctors from the allergy department on the second, third and sixth day. The responses, which are described here as positive, were responses which were classified as +, ++ and +++.

Lymphocyte Transformation Test (LTT)

A lymphocyte transformation test (LTT) was carried out as per Summer et al. [7]. Briefly, mononuclear cells of the peripheral blood (PBMC) were isolated by means of density centrifugation and stimulated for four days in four parallel formulations with different concentrations of $NiSO_4$, $CoCl_2$ or $CrCl_3$. The control stimuli were the T-cell mitogen phytohaemagglutinin (PHA, Biochrom, Berlin, Germany) 2.4 µg/ml, tetanus toxoid as the control recall antigen (TT, Chiron Behring, Berlin, Germany) 5 µg/ml. After 5 days, the PBMC were pulsed with $^3$H-thymidine and the proliferation was determined after overnight incubation by measuring the radioactivity absorbed. The results are given as a stimulation index (SI), which means the ratio of absorbed radioactivity of stimulated versus non-stimulated control cultures. An SI≥3 was deemed to be a positive response.

Polymorphism Analysis

DNA was isolated from the patient's peripheral blood with the "peqGOLD Blood DNA Mini Kit" (Peqlab, Erlangen, Germany) as per the manufacturer's protocol. The DNA obtained was diluted with distilled $H_2O$ to a final concentration of 40 ng/µl. The three polymorphisms IL-1B-3954 (rs1143634), IL-1B-31 (rs1143627), IL1-B-511 (rs16944) and the mini-satellite sequence IL-1 RN intron 2 VNTR (rs2234663) were analyzed by PCR, digest with the restriction enzymes Taq1, Alu1 or Ava1, followed by gel electrophoresis. The DNA sequences of the polymorphisms are given in Table 2.

TABLE 2

Polymorphisms analyzed and the corresponding DNA sequences

| Polymorphism | DNA Sequence |
|---|---|
| IL-1 B-3954 (rs1143634) | CTCCACATTTCAGAACCTATCTTCTT[C/T]GACACATGGATAACGAGGCTTATG (SEQ ID NO: 3) |
| 1L-1 B -511 16944(rs16944) | CTACCTTGGGTGCTGTTCTCTGCCTC[A/G]GGAGCTCTCTGTCAATTGCAGGAGC (SEQ ID NO: 4) |
| 1L-1B-31 (rs1143627) | AGCCTCCTACTTCTGCTTTTGAAAGC[C/T]ATAAAAACAGCGAGGGAGAACTGG (SEQ ID NO: 1) |
| IL-1RN intron 2 VNTR (rs2234663) | ACTCCTATTGACCTGGAGCACAGGT [(ATCCTGGGGAAAGTGAGGGAAATATGGACATCACATGGAACAACATCCAGGAGACTCAGGCCTCTAGGAGTAACTGGGTAGTGTGC)2/3/4/5/6]TTGGTTTA (SEQ ID NO: 5-9) |

The polymorphisms with their respective restriction enzymes and the resulting fragments are given in Table 3.

TABLE 3

The polymorphisms analyzed with the respective restriction enzymes and the resulting DNA fragment lengths

| Polymorphism | Restriction Enzyme | Fragment Length (bp) |
|---|---|---|
| IL-1B-3954 (rs1143634) | Taq I | T: 250 bp<br>C: 136 bp + 114 bp |
| IL-1 B-31 (rs1143627) | Alu 1 | C: 281 bp<br>T: 184 + 97 bp |
| IL-1 B-511 (rs16944) | Ava 1 | A 304 bp<br>G 189 bp + 115 bp |
| IL-1RN intron 2 VNTR (rs2234663) | Ø | Allele 1: 412 bp (4 repeats)<br>Allele 2: 240 bp (2 repeats)<br>Allele 3: 498 bp (5 repeats)<br>Allele 4: 326 bp (3 repeats)<br>Allele 5: 584 bp (6 repeats) |

Statistics

The statistical evaluation was carried out in collaboration with the Department of Statistics at Ludwig-Maximilians-Universität München with the aid of cross tabulations with exact Fisher tests with an allele model and a risk analysis (odds ratio) according to several authors [8-10].

Results

Patients with arthroplasty complications exhibited different symptoms such as pain (84.1%), followed by a reduction in their freedom of movement (78.4%), swelling (71.6%) and others. This is also reflected in the WOMAC value, where 100 points signify perfect functionality. In this case, the arthroplasty control patients confirmed the good performance of the endoprostheses with a high mean value of 82.13±18.11. On the other hand, patients with arthroplasty complications exhibited a lower mean WOMAC value of 42.06±10.12. In the group with arthroplasty complications, the rate of atopic diseases was (24.5% vs. 16.1%) higher, hay fever representing the greatest proportion (18.7% vs. 11.8%). There was also a higher number of patients with anamnesic metal hypersensitivity in the group with arthroplasty complications (24.05% vs. 9.7%). The results of the positive metal patch test were as follows: nickel 19.6% vs. 9.7%, cobalt 6.9% vs. 3.2%, chrome 2.0% vs. 1.1%. A higher number of patients were positive in the LTT. Here, 28.4% of the patients with arthroplasty complications had a positive LTT to nickel, 2.9% to cobalt, and 2.9% to chrome. Fewer patients in the control group had a positive LTT, with 19.4% to nickel, 1.1% to cobalt, and none to chrome. The results of questionnaires, patch test and LTT, are listed in Table 4.

TABLE 4

Results of questionnaires, patch test and LTT in the patient groups.
MV = mean value, SD = standard deviation

| | Arthroplasty Patients with Problems (n = 102) | | Arthroplasty Control Patients (n = 93) | |
|---|---|---|---|---|
| Problems: | 96 | 94.1% | 0 | 0% |
| Pain | 15 | 14.7% | 0 | 0% |
| Eczema | 7 | 6.9% | 0 | 0% |
| Effusion | 31 | 30.4% | 0 | 0% |
| Swelling | 73 | 71.6% | 0 | 0% |
| Loosening | 20 | 19.6% | 0 | 0% |
| Movement restriction | 80 | 78.4% | 0 | 0% |
| WOMAC value (MV ± SD) | 42.06 | ±10.12% | 92.13 | ±18.11% |
| Smoking: | | | | |
| Previously | 19 | 18.6% | 16 | 16.7% |
| Currently | 7 | 6.9% | 4 | 3.8% |
| Total | 26 | 25.5% | 20 | 20.5% |
| Atopy: | | | | |
| Atopy (total) | 25 | 24.5% | 15 | 16.1% |
| Hay fever | 19 | 18.7% | 11 | 11.8% |
| Asthma | 13 | 12.7% | 5 | 5.4% |

TABLE 4-continued

Results of questionnaires, patch test and LTT in the patient groups.
MV = mean value, SD = standard deviation

| | Arthroplasty Patients with Problems (n = 102) | | Arthroplasty Control Patients (n = 93) | |
|---|---|---|---|---|
| Atopic eczema | 0 | 0.0% | 0 | 0.0% |
| Metal hypersensitivity(anamnetic) | 25 | 24.5% | 9 | 9.7% |
| Patch test: | | | | |
| Nickel positive | 20 | 19.6% | 9 | 9.7% |
| Cobalt positive | 7 | 6.9% | 3 | 3.2% |
| Chrome positive | 2 | 2.0% | 1 | 1.1% |
| Gentamicin positive | 9 | 8.8% | 0 | 0.0% |
| Benzoyl peroxide positive | 8 | 7.8% | 2 | 2.2% |
| HEMA positive | 2 | 2.0% | 0 | 0.0% |
| N,N-Dimethyl-p-toluidine positive | 2 | 2.0% | 0 | 0.0% |
| LTT: | | | | |
| Nickel positive | 29 | 28.4% | 18 | 19.4% |
| Cobalt positive | 3 | 2.9% | 1 | 1.1% |
| Chrome positive | 3 | 2.9% | 0 | 0.0% |

There were no differences in the allele frequencies of the two different alleles C or T of the IL-1B polymorphism 3954. Neither did the subgroup analyses of patients with and without atopy, positive or negative patch test, or LTT, exhibit any relevant differences. There was a slight trend for a higher frequency of the C allele in the control group, especially with the patients without atopy, without a positive patch test or positive LTT response. The results for the IL1B polymorphism 3954 are listed in Table 5.

TABLE 5

Allele frequencies of the IL-1 B-3954 polymorphism including subgroup analyses. Results of Fisher's exact test and odds ratio (+95% confidence interval, CI) are given.

| Allele IL-1B 3954 | | Arthroplasty patients with problems (n = 102) | | Arthroplasty control patients (n = 93) | | P (Fisher's exact test) | Odds ratio [95% CI] |
|---|---|---|---|---|---|---|---|
| | | Allele Frequencies (n = 204) | [%] | Allele Frequencies (n = 186) | [%] | | |
| Overall | C | 184 | 90.2 | 174 | 95.6 | 0.050 | 0.423 [0.182-0.985] |
| | T | 86 | 42.2 | 72 | 39.6 | 0.682 | 1.113 [0.741-1.672] |
| With atopy | C | 46 | 92.0 | 28 | 93.3 | 1.000 | 0.821 [0.141-4.780] |
| | T | 22 | 44.0 | 18 | 60.0 | 0.254 | 0.524 [0.209-1.314] |
| No atopy | C | 134 | 89.3 | 146 | 96.1 | 0.028 | 0.344 [0.131-0.905] |
| | T | 62 | 41.3 | 54 | 35.5 | 0.344 | 1.279 [0.803-2.035] |
| Patch test pos. | C | 46 | 95.8 | 24 | 92.3 | 0.609 | 1.917 [0.254-14.465] |
| | T | 18 | 37.5 | 12 | 46.2 | 0.620 | 0.700 [0.266-1.842] |
| Patch test neg. | C | 138 | 88.5 | 150 | 96.2 | 0.018 | 0.307 [0.118-0.985] |
| | T | 68 | 43.6 | 60 | 38.5 | 0.420 | 1.236 [0.103-2.748] |
| LTT pos. | C | 52 | 89.7 | 32 | 94.1 | 0.705 | 0.542 [0.103-2.748] |
| | T | 30 | 51.7 | 18 | 52.9 | 1.000 | 0.925 [0.408-2.223] |
| LTT neg. | C | 94 | 87.0 | 106 | 94.6 | 0.061 | 0.380 [0.140-1.029] |
| | T | 46 | 42.6 | 38 | 33.9 | 0.212 | 1.445 [0.837-2.495] |

The IL-1B-31 polymorphism with the T allele had higher frequencies in the control group (84.3% vs. 48%). This can reflect a "protective" genotype which can reduce an immunological response to the implant. This difference in the T allele frequencies was also present in the subgroup analysis. The results of the IL-1B-31 allele frequencies are listed in Table 6.

TABLE 6

Allele frequencies of the IL-1B-31 polymorphism including the subgroup analysis. The results of Fisher's exact test and odds ratio (+95% confidence interval, CI) are given.

| Allele IL-1B-31 | | Arthroplasty patients with problems (n = 102) Allele Frequencies (n = 204) | [%] | Arthroplasty control patients (n = 93) Allele Frequencies (n = 186) | [%] | P (Fisher's exact test) | Odds ratio [95% CI] |
|---|---|---|---|---|---|---|---|
| Overall | T | 98 | 48.0 | 150 | 84.3 | 0.00000052 | 0.173 [0.106-0.281] |
|  | C | 156 | 76.5 | 112 | 62.9 | 0.005 | 1.915 [1.228-2.986] |
| With atopy | T | 18 | 36.0 | 26 | 86.7 | 0.00008 | 0.087 [0.028-0.288] |
|  | C | 42 | 84.0 | 18 | 60.0 | 0.031 | 3.500 [1.223-10.015] |
| No atopy | T | 76 | 50.7 | 124 | 83.8 | 0.0000092 | 0.199 [0.116-0.342] |
|  | C | 110 | 73.3 | 94 | 63.5 | 0.081 | 1.580 [0.965-2.586] |
| Patch test pos. | T | 24 | 50.0 | 22 | 91.7 | 0.001 | 0.091 [0.019-0.430] |
|  | C | 38 | 79.2 | 14 | 58.3 | 0.093 | 2.714 [0.932-7.909] |
| Patch test neg. | T | 74 | 47.4 | 128 | 83.1 | 0.0000003 | 0.183 [0.108-0.310] |
|  | C | 118 | 75.6 | 98 | 63.6 | 0.026 | 1.774 [1.086-2.900] |
| LTT pos. | T | 24 | 41.4 | 30 | 88.2 | 0.000008 | 0.094 [0.029-0.302] |
|  | C | 44 | 75.9 | 16 | 47.1 | 0.007 | 3.536 [1.433-8.722] |
| LTT neg. | T | 50 | 46.3 | 88 | 81.5 | 0.000001 | 0.196 [0.106-0.363] |
|  | C | 84 | 77.8 | 76 | 70.4 | 0.277 | 1.474 [0.798-2.722] |

There are no relevant differences in the allele frequencies of the IL-1B-511 polymorphism. There was a trend for a higher frequency of the C allele of this polymorphism in the control group, but this was not high enough to be statistically significant. The results for the IL-1 B-511 polymorphism are listed in Table 7.

TABLE 7

Allele frequencies of the IL-1B-511 polymorphism including the subgroup analysis. The results of Fisher's exact test and odds ratio (+95% confidence interval, CI) are given.

| Allele IL-1B 511 | | Arthroplasty patients with problems (n = 102) Allele Frequencies (n = 204) | [%] | Arthroplasty control patients (n = 93) Allele Frequencies (n = 186) | [%] | P (Fisher's exact test) | Odds ratio [95% CI] |
|---|---|---|---|---|---|---|---|
| Overall | C | 150 | 73.5 | 158 | 87.8 | 0.0005 | 0.387 [0.225-0.666] |
|  | T | 130 | 63.7 | 106 | 58.9 | 0.346 | 1.226 [0.812-1.851] |
| With atopy | C | 30 | 60.0 | 22 | 73.3 | 0.333 | 0.545 [0.203-1.464] |
|  | T | 36 | 72.0 | 18 | 60.0 | 0.327 | 1.714 [0.659-1.675] |
| No atopy | C | 116 | 77.3 | 136 | 90.7 | 0.003 | 0.351 [0.180-0.686] |
|  | T | 90 | 60.0 | 88 | 58.7 | 0.906 | 1.057 [0.667-1.675] |
| Patch test pos. | C | 34 | 70.8 | 24 | 92.3 | 0.040 | 0.202 [0.042-0.974] |
|  | T | 30 | 62.5 | 16 | 61.5 | 1.000 | 1.042 [0.390-2.783] |
| Patch test neg. | C | 116 | 74.4 | 134 | 87.8 | 0.006 | 0.433 [0.240-0.782] |
|  | T | 100 | 64.1 | 90 | 58.4 | 0.351 | 1.270 [0.803-2.007] |
| LTT pos. | C | 40 | 69.0 | 30 | 88.2 | 0.044 | 0.296 [0.091-0.966] |
|  | T | 38 | 65.5 | 20 | 58.8 | 0.655 | 1.330 [0.556-3.180] |
| LTT neg. | C | 82 | 75.9 | 98 | 87.5 | 0.035 | 0.451 [0.221-0.919] |
|  | T | 70 | 64.8 | 72 | 64.3 | 1.000 | 1.023 [0.589-1.778] |

With IL-1B-RN-intron-2-VNTR there was a much higher risk of arthroplasty problems which correlated with the allele 3 (498 bp, 5 repeats). This risk was increased when the patients had an additional atopic disease. This risk did not correlate with the patch test response or the LTT reactivity. The results for the IL-1B-RN intron 2 VNTR are listed in Table 8.

TABLE 8

Allele frequencies of the IL-1B-RN-VNTR polymorphism including the subgroup analysis. The results of Fisher's exact test and odds ratio (+95% confidence interval, CI) are given.

| Allele IL-1B RN VNTR | | Arthroplasty patients with problems (n = 102) Allele Frequencies (n = 204) | [%] | Arthroplasty control patients (n = 93) Allele Frequencies (n = 186) | [%] | P (Fisher's exact test) | Odds ratio [95% CI] |
|---|---|---|---|---|---|---|---|
| Overall | 240 bp | 48 | 27.6 | 44 | 28.2 | 0.903 | 0.970 [0.599-1.570] |
|  | 326 bp | 6 | 3.4 | 6 | 3.8 | 1.000 | 0.905 [0.289-2.865] |
|  | 412 bp | 128 | 72.7 | 136 | 86.1 | 0.030 | 0.431 [0.247-0.755] |
|  | 498 bp | 86 | 49.4 | 36 | 22.8 | 0.0000475 | 3.312 [2.058-5.331] |
|  | 595 bp | 6 | 3.4 | 0 | 0.0 | 0.031 | 0515 [0.464-0.573] |
| With atopy | 240 bp | 8 | 19.0 | 10 | 33.3 | 0.182 | 0.471 [0.160-1.138] |
|  | 326 bp | 0 | 0.0 | 2 | 6.7 | 0.170 | 0.400 [0.300-0.533] |
|  | 412 bp | 30 | 71.4 | 28 | 93.3 | 0.032 | 0.179 [0.037-0.870] |
|  | 498 bp | 36 | 85.7 | 4 | 13.3 | 0.00000001 | 39.000 [9.990-152.257] |
|  | 595 bp | 2 | 4.8 | 0 | 0.0 | 0.507 | 0.571 [0.467-0.700] |
| No atopy | 240 bp | 40 | 31.3 | 34 | 27.0 | 0.491 | 1.230 [0.715-2.116] |
|  | 326 bp | 6 | 4.7 | 4 | 3.1 | 0.749 | 1.525 [0.420-5.536] |
|  | 412 bp | 94 | 72.3 | 108 | 84.4 | 0.023 | 0.484 [0.262-0.892] |
|  | 498 bp | 50 | 39.1 | 32 | 25.0 | 0.022 | 1.923 [1.126-3.283] |
|  | 595 bp | 4 | 3.1 | 0 | 0.0 | 0.122 | 0.492 [0.434-0.558] |
| Patch test pos. | 240 bp | 4 | 9.1 | 2 | 11.1 | 1.000 | 0.800 [0.133-4.809] |
|  | 326 bp | 0 | 0 | 0 | 0 | n.d. | n.d. |
|  | 412 bp | 34 | 77.3 | 18 | 90.0 | 0.312 | 0.378 [0.075-1.913] |
|  | 498 bp | 26 | 59.1 | 4 | 20.0 | 0.006 | 5.778 [1.656-20.159] |
|  | 595 bp | 2 | 4.5 | 0 | 0 | 1.000 | 0.677 [0.571-0.804] |
| Patch test neg. | 240 bp | 44 | 33.8 | 42 | 30.4 | 0.601 | 1.169 [0.700-1.954] |
|  | 326 bp | 6 | 4.6 | 6 | 4.3 | 1.000 | 1.065 [0.334-3.388] |
|  | 412 bp | 94 | 71.2 | 118 | 85.4 | 0.005 | 0.419 [0.229-0.768] |
|  | 498 bp | 60 | 46.2 | 32 | 23.2 | 0.0001 | 2.839 [1.680-4.798] |
|  | 595 bp | 4 | 3.1 | 0 | 0 | 0.054 | 0.477 [0.421-0.541] |
| LTT pos. | 240 bp | 8 | 16.7 | 4 | 14.3 | 1.000 | 1.200 [0.326-4.414] |
|  | 326 bp | 4 | 8.3 | 0 | 0 | 0.290 | 0.611 [0.508-0.735] |
|  | 412 bp | 38 | 76.0 | 26 | 92.2 | 0.073 | 0.244 [0.050-1.180] |
|  | 498 bp | 30 | 62.5 | 6 | 21.4 | 0.001 | 6.111 [2.085-17.911] |
|  | 595 bp | 0 | 0 | 0 | 0 | n.d. | n.d. |
| LTT neg. | 240 bp | 30 | 31.3 | 32 | 32.0 | 1.000 | 0.966 [0.529-1.764] |
|  | 326 bp | 2 | 2.1 | 6 | 5.9 | 0.281 | 0.340 [0.067-1.729] |
|  | 412 bp | 72 | 75.0 | 84 | 82.4 | 0.227 | 0.643 [0.323-1.278] |
|  | 498 bp | 44 | 45.8 | 24 | 23.5 | 0.001 | 2.750 [1.496-5.055] |
|  | 595 bp | 2 | 2.1 | 0 | 0 | 0.234 | 0.480 [0.415-0.555] |

LIST OF REFERENCES

1. Sharkey P F et al. Why are total knee arthroplasties failing today. J Arthroplasty 2017; 29:1774-1778.
2. Thomsen M et al. Adverse Reaktionen gegenüber orthopädisch-chirurgischen Metallimplantaten nach Kniegelenkersatz. Hautarzt 2016; 67:347-351.
3. Granchi D et al. Sensitivity to implant materials in patients undergoing total hip replacement. J Biomed Mater Res B Appl Biomater 2006; 77(2):257-64.
4. Thomas P, Summer B. Diagnosis and management of patients with allergy to metal implants. Exp Rev Clin Immunol. 2015; 11(4):501-509.
5. Stucki G et al. Evaluation einer deutschen Version des WOMAC (Western Ontario and McMaster Universities) Arthroseindex. Z Rheumatol 1996; 55(1):40-49.
6. Schnuch A et al. Durchführung des Epikutantests mit Kontaktallergenen. Leitlinie der Deutschen Dermatologischen Gesellschaft und der Deutschen Gesellschaft für Allergie und klinische Immunologie. JDDG 2008; 6(9): 770-775.
7. Summer B et al. Nickel (Ni) allergic patients with complications to Ni containing joint replacement show preferential IL-17 type reactivity to Ni. Contact Dermatitis 2010; 63:15-22.
8. Colhoun H M et al. Problems of reporting genetic associations with complex outcomes. Lancet. 2003; 361 (9360):865-72.
9. Yang H et al. Association of interleukin gene polymorphisms with the risk of coronary artery disease. Genetics and molecular research: GMR. 2015; 14(4):12489-96.
10. Lopez-Mejias R et al. Interleukin 1 beta (IL1ss) rs16944 genetic variant as a genetic marker of severe renal manifestations and renal sequelae in Henoch-Schonlein purpura. Clinical and experimental rheumatology. 2016; 34(3 Suppl 97):S84-8.
11. den Dunnen et al., HGVS Recommendations for the Description of Sequence Variants: 2016 Update, HUMAN MUTATION, Vol. 37, No. 6, 564-569, 2016, doi10.1002/humu.22981.

The present invention is not limited to embodiments described herein; reference should be had to the appended claims.

What is claimed is:

1. A method to predict an increased risk of a metal implant sensitivity in a test person, the method comprising:
   providing an isolated sample comprising genetic material of the test person;
   analyzing the genetic material of the test person to detect a number of repeats of SEQ ID NO: 2 in the VNTR polymorphism rs2234663 in the interleukin-1 receptor antagonist (IL-1RN) gene;
   detecting the presence of a five repeat allele of rs2234663;
   determining that an increased risk to a metal implant sensitivity in the test person is present; and
   implanting an implant into the test person, wherein the implant is a ceramic material.

2. The method as recited in claim 1, wherein the increased risk to the metal implant sensitivity is a greater inflammation sensitivity.

3. The method as recited in claim 1, further comprising: determining a possible presence of an atopic disease.

4. The method as recited in claim 3, wherein the atopic disease is selected from allergic bronchial asthma, allergic rhinitis and atopic dermatitis.

* * * * *

SEQUENCE LISTING

<160> NUMBER OF SEQ ID NOS: 13

<210> SEQ ID NO 1
<211> LENGTH: 51
<212> TYPE: DNA
<213> ORGANISM: Homo sapiens
<220> FEATURE:
<223> OTHER INFORMATION: rs1143627

<400> SEQUENCE: 1
agcctcctac ttctgctttt gaaagcyata aaaacagcga gggagaactg g            51

<210> SEQ ID NO 2
<211> LENGTH: 86
<212> TYPE: DNA
<213> ORGANISM: Homo sapiens
<220> FEATURE:
<223> OTHER INFORMATION: rs2234663 repeat

<400> SEQUENCE: 2
atcctgggga aagtgaggga aatatggaca tcacatggaa caacatccag gagactcagg   60
cctctaggag taactgggta gtgtgc                                        86

<210> SEQ ID NO 3
<211> LENGTH: 52
<212> TYPE: DNA
<213> ORGANISM: Homo sapiens
<220> FEATURE:
<223> OTHER INFORMATION: rs1143634

<400> SEQUENCE: 3
ctccacattt cagaacctat cttcttygac acatgggata acgaggctta tg           52

<210> SEQ ID NO 4
<211> LENGTH: 52
<212> TYPE: DNA
<213> ORGANISM: Homo sapiens
<220> FEATURE:
<223> OTHER INFORMATION: rs16944

<400> SEQUENCE: 4
ctaccttggg tgctgttctc tgcctcrgga gctctctgtc aattgcagga gc           52

<210> SEQ ID NO 5
<211> LENGTH: 205
<212> TYPE: DNA
<213> ORGANISM: Homo sapiens
<220> FEATURE:
<223> OTHER INFORMATION: rs2234663 two repeats

<400> SEQUENCE: 5
actcctattg acctggagca caggtatcct ggggaaagtg agggaaatat ggacatcaca   60
tggaacaaca tccaggagac tcaggcctct aggagtaact gggtagtgtg catcctgggg  120
aaagtgaggg aaatatggac atcacatgga acaacatcca ggagactcag gcctctagga  180
gtaactgggt agtgtgcttg gttta                                        205

<210> SEQ ID NO 6
<211> LENGTH: 291
<212> TYPE: DNA
<213> ORGANISM: Homo sapiens
<220> FEATURE:
<223> OTHER INFORMATION: rs2234663 three repeats

<400> SEQUENCE: 6

```
actcctattg acctggagca caggtatcct ggggaaagtg agggaaatat ggacatcaca     60
tggaacaaca tccaggagac tcaggcctct aggagtaact gggtagtgtg catcctgggg    120
aaagtgaggg aaatatggac atcacatgga acaacatcca ggagactcag gcctctagga    180
gtaactgggt agtgtgcatc ctggggaaag tgagggaaat atggacatca catggaacaa    240
catccaggag actcaggcct ctaggagtaa ctgggtagtg tgcttggttt a             291
```

```
<210> SEQ ID NO 7
<211> LENGTH: 377
<212> TYPE: DNA
<213> ORGANISM: Homo sapiens
<220> FEATURE:
<223> OTHER INFORMATION: rs2234663 four repeats

<400> SEQUENCE: 7
```

```
actcctattg acctggagca caggtatcct ggggaaagtg agggaaatat ggacatcaca     60
tggaacaaca tccaggagac tcaggcctct aggagtaact gggtagtgtg catcctgggg    120
aaagtgaggg aaatatggac atcacatgga acaacatcca ggagactcag gcctctagga    180
gtaactgggt agtgtgcatc ctggggaaag tgagggaaat atggacatca catggaacaa    240
catccaggag actcaggcct ctaggagtaa ctgggtagtg tgcatcctgg ggaaagtgag    300
ggaaatatgg acatcacatg gaacaacatc caggagactc aggcctctag gagtaactgg    360
gtagtgtgct tggttta                                                  377
```

```
<210> SEQ ID NO 8
<211> LENGTH: 463
<212> TYPE: DNA
<213> ORGANISM: Homo sapiens
<220> FEATURE:
<223> OTHER INFORMATION: rs2234663 five repeats

<400> SEQUENCE: 8
```

```
actcctattg acctggagca caggtatcct ggggaaagtg agggaaatat ggacatcaca     60
tggaacaaca tccaggagac tcaggcctct aggagtaact gggtagtgtg catcctgggg    120
aaagtgaggg aaatatggac atcacatgga acaacatcca ggagactcag gcctctagga    180
gtaactgggt agtgtgcatc ctggggaaag tgagggaaat atggacatca catggaacaa    240
catccaggag actcaggcct ctaggagtaa ctgggtagtg tgcatcctgg ggaaagtgag    300
ggaaatatgg acatcacatg gaacaacatc caggagactc aggcctctag gagtaactgg    360
gtagtgtgca tcctggggaa agtgagggaa atatggacat cacatggaac aacatccagg    420
agactcaggc ctctaggagt aactgggtag tgtgcttggt tta                     463
```

```
<210> SEQ ID NO 9
<211> LENGTH: 549
<212> TYPE: DNA
<213> ORGANISM: Homo sapiens
<220> FEATURE:
<223> OTHER INFORMATION: rs2234663 six repeats

<400> SEQUENCE: 9
```

```
actcctattg acctggagca caggtatcct ggggaaagtg agggaaatat ggacatcaca     60
tggaacaaca tccaggagac tcaggcctct aggagtaact gggtagtgtg catcctgggg    120
aaagtgaggg aaatatggac atcacatgga acaacatcca ggagactcag gcctctagga    180
gtaactgggt agtgtgcatc ctggggaaag tgagggaaat atggacatca catggaacaa    240
```

```
catccaggag actcaggcct ctaggagtaa ctgggtagtg tgcatcctgg ggaaagtgag    300
ggaaatatgg acatcacatg gaacaacatc caggagactc aggcctctag gagtaactgg    360
gtagtgtgca tcctggggaa agtgagggaa atatggacat cacatggaac aacatccagg    420
agactcaggc ctctaggagt aactgggtag tgtgcatcct ggggaaagtg agggaaatat    480
ggacatcaca tggaacaaca tccaggagac tcaggcctct aggagtaact gggtagtgtg    540
cttggttta                                                            549

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
tcttttcccc tttcctttaa ct                                              22

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
gagagactcc cttagcacct agt                                             23

<210> SEQ ID NO 12
<211> LENGTH: 17
<212> TYPE: DNA
<213> ORGANISM: Artificial Sequence
<220> FEATURE:
<223> OTHER INFORMATION: Primer

<400> SEQUENCE: 12
cccctcagca acactcc                                                    17

<210> SEQ ID NO 13
<211> LENGTH: 17
<212> TYPE: DNA
<213> ORGANISM: Artificial Sequence
<220> FEATURE:
<223> OTHER INFORMATION: Primer

<400> SEQUENCE: 13
ggtcagaagg gcagaga                                                    17
```